United States Patent
Gord (12)

(10) Patent No.: US 6,181,969 B1
(45) Date of Patent: Jan. 30, 2001

(54) PROGRAMMABLE CURRENT OUTPUT STIMULUS STAGE FOR IMPLANTABLE DEVICE

(75) Inventor: John C. Gord, Venice, CA (US)

(73) Assignee: Advanced Bionics Corporation, Sylmar, CA (US)

( * ) Notice: Under 35 U.S.C. 154(b), the term of this patent shall be extended for 0 days.

(21) Appl. No.: 09/338,700

(22) Filed: Jun. 23, 1999

Related U.S. Application Data

(60) Provisional application No. 60/090,833, filed on Jun. 26, 1998.

(51) Int. Cl.$^7$ ............................................. A61N 1/36
(52) U.S. Cl. .................................. 607/59; 607/57
(58) Field of Search ................... 607/9, 29, 30, 607/34, 56, 97, 99

(56) References Cited

U.S. PATENT DOCUMENTS

| | | | |
|---|---|---|---|
| 4,532,930 | * 8/1985 | Crosby et al. | 607/57 |
| 4,592,359 | 6/1986 | Galbraith | 128/419 |
| 4,671,288 | 6/1987 | Gough | 128/635 |
| 5,193,539 | 3/1993 | Schulman et al. | 128/419 |
| 5,336,937 | 8/1994 | Sridhar et al. | 307/201 |
| 5,497,113 | 3/1996 | Uber | 327/170 |
| 5,522,865 | 6/1996 | Schulman et al. | 607/56 |
| 5,574,633 | 11/1996 | Prater | 363/59 |
| 5,603,726 | 2/1997 | Schulman et al. | 607/57 |

FOREIGN PATENT DOCUMENTS

| | | |
|---|---|---|
| 0305980 | 8/1989 | (EP) . |
| 0598617 | 5/1994 | (EP) . |
| 9725778 | 7/1997 | (WO) . |

\* cited by examiner

Primary Examiner—William E. Kamm
(74) Attorney, Agent, or Firm—Bryant R. Gold

(57) ABSTRACT

A programmable output current source for use within an implantable tissue or nerve stimulator, e.g., an implantable cochlear stimulator or spinal cord stimulator, includes parallel-connected P-FET current source sets connected between a positive voltage rail and an electrode node, and parallel-connected N-FET current source sets connected between the electrode node and a negative voltage rail. The N-FET current source sets include n N-FET current sources, where n is an integer 0, 1, 2, 3, 4, . . . , and wherein each N-FET current source, when enabled, respectively sinks a current $2^n I$ from the electrode node to the negative rail, where I is a selectable fixed current. Similarly, the P-FET current source sets include n P-FET current sources, where n=0, 1, 2, 3, . . . n, and wherein each P-FET current source, when enabled, respectively sources a current $2^n I$ from the positive voltage rail to the electrode node. An individual current pulse is formed by selecting an electrode pair, and enabling a desired combination of P-FET current sources so that a desired total current is sourced to one of the electrodes of the selected electrode pair, and at the same time enabling a corresponding combination of N-FET current sources so that the same total current is sunk from the other electrode of the selected electrode pair. Sequences of current pulses, e.g., biphasic or multiphasic stimulation pulse pairs, are formed by combining individual current pulses having the desired polarity and timing relationship.

20 Claims, 14 Drawing Sheets

PROGRAMMABLE CURRENT OUTPUT STIMULUS STAGE FOR IMPLANTABLE DEVICE

This application claims the benefit of U.S. Provisional Application Ser. No. 60/090,833, filed Jun. 26, 1998.

BACKGROUND OF THE INVENTION

The present invention relates to implantable medical devices, and more particularly to the output stage of an implantable electrical stimulator. Even more particularly, the invention relates to a programmable output current source for use within an implantable tissue or nerve stimulator, e.g., an implantable cochlear stimulator.

In the implantable medical device field, a medical device, configured to perform a desired medical function, is implanted in the living tissue of a patient so that a desired function may be carried out as needed for the benefit of the patient. Numerous examples of implantable medical devices are known in the art, ranging, from implantable pacemakers, cochlear stimulators, spinal cord stimulators, muscle stimulators, glucose sensors, and the like.

Some implantable medical devices are configured to perform the stimulating function, i.e., to generate an electrical signal, typically a biphasic current pulse, that is applied to body tissue or to a nerve, for the purpose of causing a desired muscle contraction, or activating a desired nerve. Examples of medical devices that perform the stimulating function are shown, e.g., in U.S. Pat. Nos. 5,193,539 and 5,603,726, both of which patents are incorporated herein by reference. The present invention is directed to such implantable stimulating devices.

Other medical devices are configured to perform the sensing function, i.e., to sense a particular parameter, e.g., the amount of a specified substance in the blood or tissue of the patient, and to generate an electrical signal indicative of the quantity or concentration level of the substance sensed. An example of an implantable medical device that performs the sensing function is shown, e.g., in U.S. Pat. No. 4,671,288. Sometimes, sensing a desired parameter or other element, e.g., an evoked response, occurs through the same or similar electrodes through which stimulation is applied.

Some stimulating devices, e.g., cardiac pacemakers, and the microstimulators of the type disclosed in the above-referenced '539 patent, may always apply their stimulation pulses through the same electrodes. Other stimulating devices, e.g., cochlea stimulators of the type disclosed in the above-referenced '726 patent, however, apply the stimulus pulses, which are of varying amplitude and polarity, to different electrodes, or different electrode pairs, as a function of the sensed input signal. There is thus a need in the implantable stimulating device field to provide an output circuit for use with such devices that allows different electrode pairs to be selected through which stimulus currents having different amplitudes and polarities may be applied.

As medical devices have become more useful and numerous in recent years, there is a continual need to provide very low power sensors and stimulators that may be connected to, or incorporated within, such devices so that the desired function of the device can be carried out without the expenditure of large amounts of power (which power, for an implanted device, is usually limited). Moreover, there is a constant need and desire to make such implantable devices smaller and smaller.

To meet this need (smaller circuits, less power) within an implantable stimulating device, it has been common to design an output circuit for interfacing with the electrodes which selectively connects a single current source, or one of a plurality of current sources, to a selected electrode pair, rather than designing a separate current source for each electrode pair. In order to allow the polarity of the stimulus applied through the selected electrode pair to be changed without requiring an additional current source, which would tend to make the device larger and consume more power, it is also known to employ a switching matrix which selectively connects the selected electrode pair to either side of the current source, or which otherwise causes the current flow direction through the selected electrode pair to change. All such switching matrices, or equivalent schemes, require that the electrode nodes (those nodes connected directly to a given electrode) be physically or electrically switched from one circuit location to another. Disadvantageously, such "switching" requires additional circuitry which not only increases the impedance of the circuit connection path, but which also, during operation, takes time to complete, i.e., takes a finite time to switch the switching components from being biased ON (low impedance) or OFF (high impedance) so that the desired "connection" may be established or disconnected.

There is thus a need in the art for an output circuit useable within an implantable current stimulator that is small, operates at low power, and does not physically or electrically switch the electrode node from one circuit location to another as different and continually changing stimulus parameters (amplitude, polarity, electrode pairings) are needed.

SUMMARY OF THE INVENTION

The present invention addresses the above and other needs by providing a programmable output current source for use within an implantable tissue or nerve stimulator, e.g., an implantable cochlear stimulator, that does not switch a current or voltage source between different electrode pairs. Rather, each electrode node has parallel-connected P-FET current source sets permanently connected between it (the electrode node) and a positive voltage rail, and parallel-connected N-FET current source sets permanently connected between it (the electrode node) and a negative voltage rail. The P-FET current sources provide a programmable amount of current to the electrode node (i.e., the P-FET current sources "source" current to the electrode node) and the N-FET current sources receive the programmable amount of current from the electrode node (i.e., the N-FET current source "sink" current from the electrode node). It is thus never necessary to physically or electronically "switch" the electrode nodes between one or more circuit locations, or to "switch" the electrode node to a different side of a current or voltage source so as to change the polarity of the stimulus (current) flowing through the electrode node.

In accordance with one aspect of the invention, complementary sets of CMOS P-FET and N-FET current sources are fabricated on a semiconductor substrate in a relatively small area so as to be permanently connected to an electrode node. Such current sources operate at very low power levels, and when disabled (turned OFF) do not consume any power.

In accordance with another aspect of the invention, such P-FET and N-FET current source sets source or sink increasing amounts of current for each electrode node. That is, for example, a first P-FET current source included as part of the P-FET current source sets generates (sources), when enabled, a current of I to the electrode node, where I is a fixed, selectable current value; a second P-FET current source sources, when enabled, a current 2I to the electrode node; a third P-FET current source sources, when enabled, sources a current 3I to the electrode node; and so on, for up to n P-FET current sources, where n is an integer of n=0, 1, 2, 3, . . . n. In this manner, it is seen that each of the n P-FET current sources respectively generates (sources) a current of $2^n$I to the electrode node when enabled. Similarly, there are n N-FET current sources, each of which respectively generates (sinks) a current of $2^n$I from the electrode node.

In accordance with an additional aspect of the invention, sequences of current pulses, e.g., biphasic or multiphasic stimulation pulse pairs, are formed by combining individual current pulses having the desired polarity and timing relationship.

To illustrate this process, consider a biphasic pulse that is to be applied between electrodes 5 and 6 of sixteen electrodes. The biphasic pulse is to have a positive pulse having an amplitude of 3I for 33 μsec, followed by a negative pulse of 3I for 33 μsec. Such biphasic pulse is formed, using the present invention, by simply enabling the first and second P-FET current sources (n=1 and n=2) permanently connected to the 5th electrode node at the same time that the first and second N-FET current sources (n=1 and n=2) are enabled that are permanently connected to the 6th electrode node. This action causes a current of I (from the first current source) plus 2I (from the second current source), making a combined total of 3I, to be sourced to the 5th electrode node at the same time that a current 3I is also sunk from the 6th electrode node, thereby creating the first half of the desired biphasic pulse.

After the desired duration of the first half of the biphasic pulse, e.g., after 33 μsec, the first and second P-FET current sources permanently connected to the 5th electrode node are disabled (turned OFF), and the first and second N-FET current sources permanently connected to the 5th electrode node are enabled. Likewise, at this same time, the first and second N-FET current sources permanently connected to the 6th electrode node are disabled, and the first and second P-FET current sources permanently connected to the 6th electrode node are enabled. This action causes a current of I (from the first current source) plus 2I (from the second current source), making a combined total of 3I, to be sourced to the 6th electrode node at the same time that a current 3I is also sunk from the 5th electrode node, thereby creating the second half of the desired biphasic pulse.

After the desired duration of the second half of the biphasic pulse, e.g., after 33 μsec, all current sources are disabled, thereby ending the biphasic stimulation pulse.

In one embodiment of the invention, the programmable amplitude of the current pulse may be further refined or enhanced by also providing an additional m P-FET and m N-FET current sources as part of the P-FET and N-FET current source sets which are permanently connected to each electrode pair. Such additional m P-FET and m N-FET current sources respectively source or sink a current $1/2^m$ to or from the electrode node, where m is an integer, m=1, 2, 3, . . . m. Such additional current sources provide the ability to program the amplitude of the current pulse applied between a selected pair of electrodes to assume integer and/or fractional values of I, e.g., I/2,I/4,I/8, 5I/4, 7I/2, and the like. Such feature is particularly advantageous when the value of I is fixed, or limited to only a discrete number of values, e.g., four values, as is commonly the case within an implantable stimulating device.

It is thus a feature of the invention to provide an output current source circuit for each electrode of an implantable tissue or nerve stimulator that can selectively source or sink a current having a programmable amplitude to the electrode node while at all times remaining permanently connected to the electrode node.

It is a further feature of the invention to provide such an output current source circuit that may be fabricated using low power CMOS N-FET and P-FET transistors.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
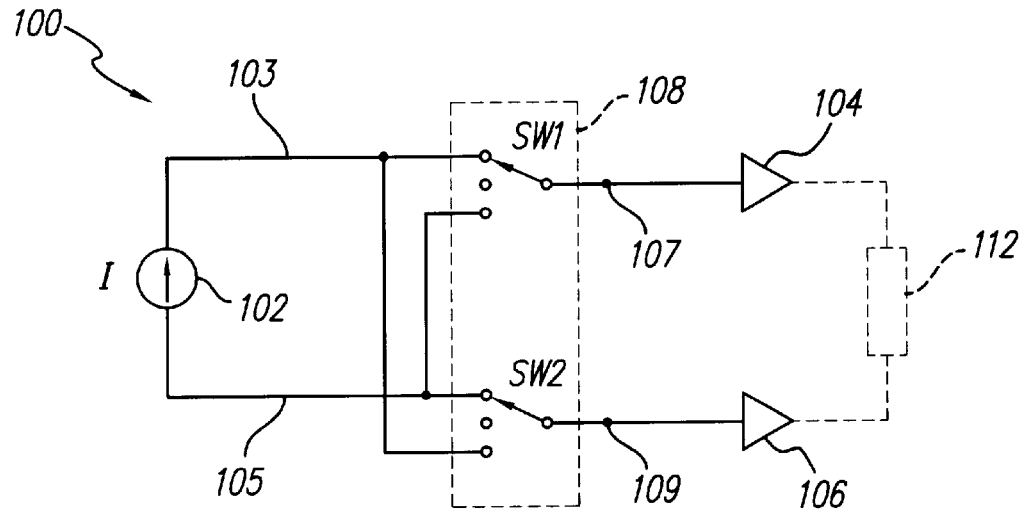
FIG. 1 shows a functional diagram of a conventional (prior art) output circuit for use with a single polarity current source.

To better understand the present invention, and in particular to better appreciate one of the problems that the present invention solves, reference is made to FIG. 1, where there is shown a functional diagram of a conventional (prior art) output circuit 100 for use with a single polarity current source 102. The single polarity current source 102 has a forward path 103 which sources current, and a return path 105 which sinks current. The single polarity current source is desirable, according to the teachings of the prior art, because its polarity is fixed, and it reduces the number of components required for its implementation. However, in order to connect such single polarity current source to a pair of electrodes 104 and 106, it is necessary to use a switching matrix 108 having multiple switches therein. Two such switches SW1 and SW2 are shown, for illustrative purposes, within the switching matrix 108 of FIG. 1

As seen in FIG. 1, the electrodes 104 and 106 connect with a load 112, which load is typically body tissue or fluids. For the position or setting of switches SW1 and SW2 shown in FIG. 1, where each is connected to its respective "top" position (as illustrated in FIG. 1), the forward current path 103 from current source 102 is connected to electrode 104, thereby causing electrode 104 to function as a source electrode, and the return current path 105 is connected to electrode 106, thereby causing electrode 106 to function as a sink (or return) electrode. Hence, with this setting, the current I flows from electrode 104, through the load 112, to the electrode 106.

In order to reverse the current flow direction through the load 112, it is necessary to switch SW1 and SW2 within the switching matrix 108 to their respective bottom positions (as shown in FIG. 1). Such positions connect the return path 105 of current source 102 to electrode 104, and the forward path 103 of current source 102 to electrode 106, thereby causing the current I to flow from electrode 106, through the load 112, to the electrode 104.

If electrodes 104 and 106 are not to be used, then it is necessary for the switching matrix 108 to be set such that the switches SW1 and SW2 are in their respective middle positions. As shown in FIG. 1, the middle positions cause electrodes 104 and 106 to "float", without being connected to either the return current path 105 or the forward current path 103 of the current source 102. In some embodiments, the middle position may be grounded, and/or may short the two electrodes 104 and 106 to each other.

That which is shown in FIG. I is greatly simplified. That is, many implantable devices have many more electrodes than two, including one or more reference electrodes to permit selective monopolar or bipolar simulation. Further, such devices may utilize more than a single current source. In such an instance, the output switching matrix 108 becomes much more complicated, and may include more functional switches than the two switches SW1 and SW2 which are depicted. Every time a different electrode configuration is desired, or every time a change in polarity of the stimulation current is desired, the switches within the switching matrix must be appropriately set. With each different setting of the output switch matrix 108, the electrode node 107 (that node within the implanted circuitry 100 which directly connects with electrode 104) and the electrode node 109 (that node within the implanted circuitry 100 which directly connects with electrode 106) must be connected to a new circuit location.

Figures 1, 2:
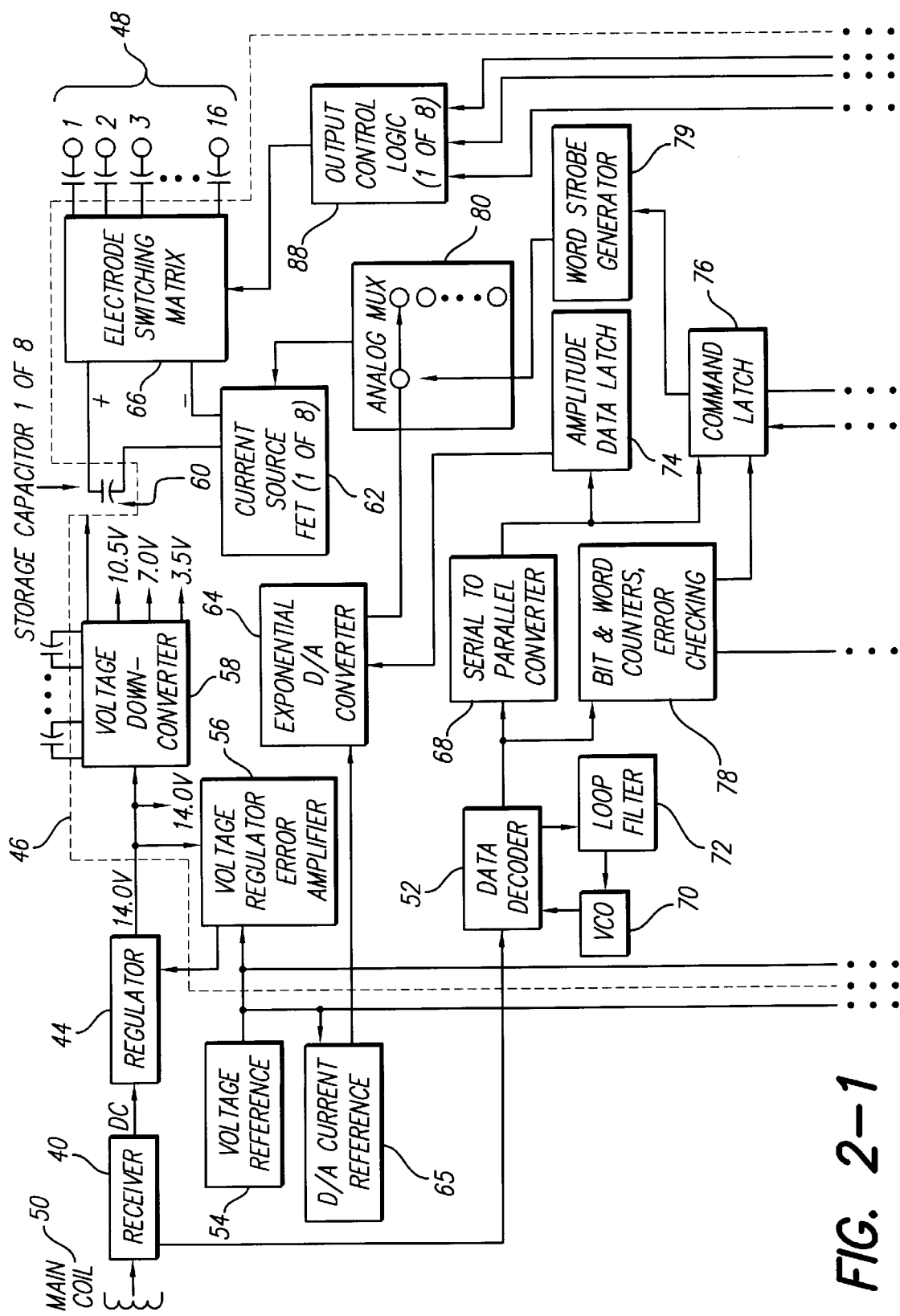
FIG. 2 is a block diagram of a cochlear stimulation system of the type described in the previously-referenced U.S. Pat. No. 5,522,865.
Figure 2:
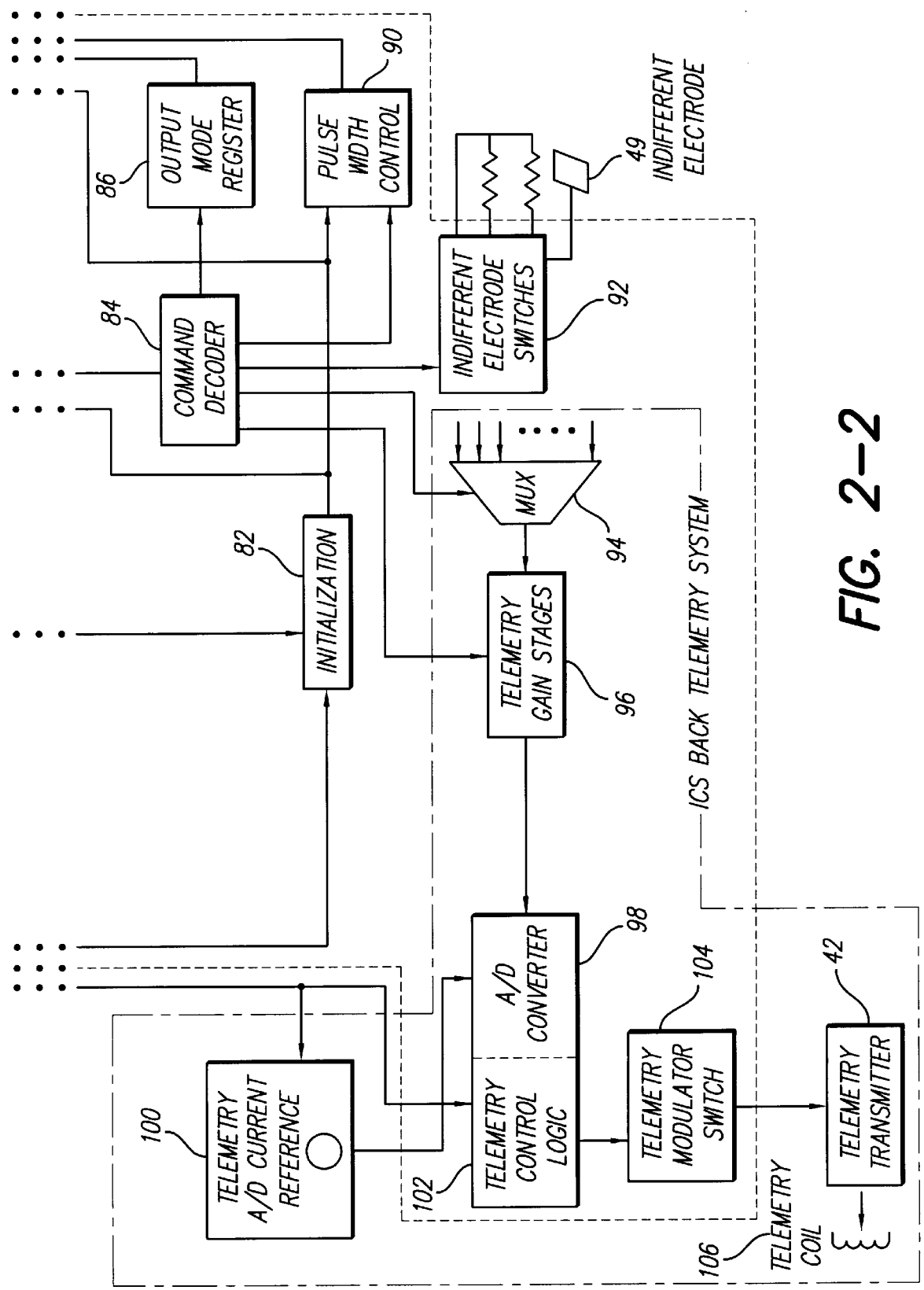

With reference to FIG. 2, there is shown a block diagram of a cochlear stimulation system of the type described in the previously-referenced U.S. Pat. No. 5,522,865, incorporated herein by reference. The blocks and elements shown in FIG. 2 are described in the '865 patent. Note, for the system shown in FIG. 2, the electrode switching matrix 66, in cooperation with the indifferent electrode swithces 92, selectively connects a pair of electrodes, which may include the indifferent electrode 49, to one of eight current sources 62. Such connection requires the use of many switches within the switching matrix 66 and the indifferent electrode switches 92, which switches selectively connect the respective electrode nodes to the desired circuit locations.

In contrast to the switching matrix approach shown in FIGS. 1 and 2, the present invention advantageously eliminates the output switching matrix altogether, and provides a programmable current output circuit that leaves the electrode node permanently attached to a fixed location within the output circuit. Such non-switching approach is achieved at the cost of more circuit components, but is ameliorated by the fact that the additional circuit components may be fabricated in a relatively small area on a semiconductor wafer, and are repetitious (comprising the same CMOS N-FET or P-FET components repeated over and over again). These factors make fabrication of such programmable current output circuit on a silicon wafer a manageable and cost-effective approach.

Figure 3:
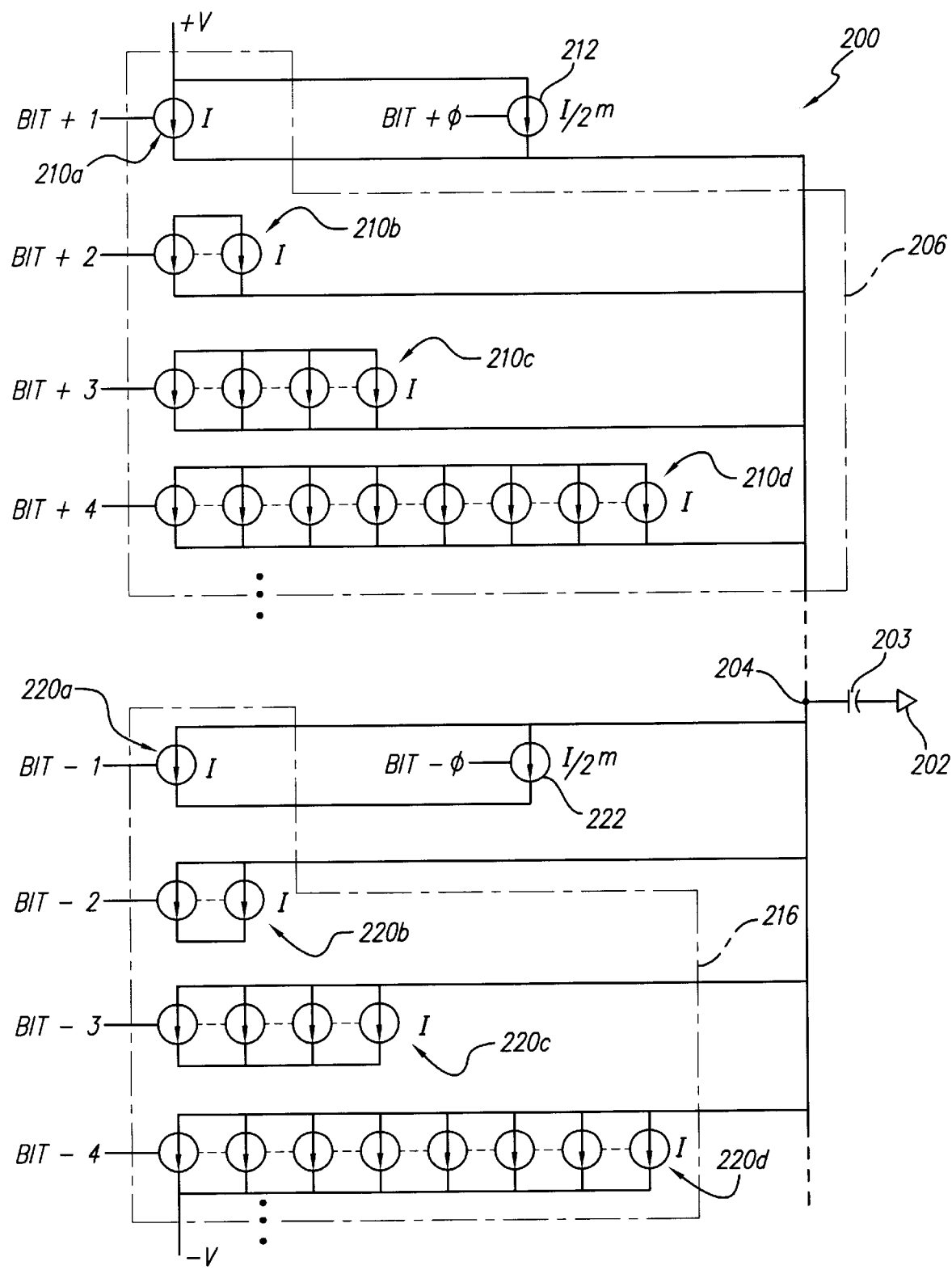
FIG. 3 is a functional diagram of a programmable output current circuit that is permanently connected to an electrode node of an implantable stimulating device in accordance with the teachings of the present invention.

Turning next to FIG. 3, a functional diagram of a programmable output current circuit 200 made in accordance with the present invention is shown. It is to be emphasized that the circuit shown in FIG. 3 is a functional diagram, used to teach the manner used by the invention to achieve a programmable current source that is permanently connected to an electrode node without an intervening electrode switching matrix. The output current circuit 200 shown in FIG. 3 is repeated for each electrode used by the implantable device. Thus, for example, if the implantable stimulator device includes 16 stimulus electrodes, then the circuit 200 shown in FIG. 3 is repeated sixteen times, once for each electrode.

As seen in FIG. 3, a programmable output current circuit 200 includes an electrode 202 which is permanently connected to an electrode node 204 through a coupling capacitor 203. The electrode node 204 is permanently connected to a set 206 of n P-FET current sources 210a, 210b, 210c, 210d, . . . 210n, where n is an integer equal to 0, 1, 2, . . . Each of the n P-FET current sources 210 comprises n individual current sources connected in parallel, each configured to source a current I. That is, a first current source 210a comprises a single current source configured to source a current I. A second current source 210b comprises two current sources connected in parallel, each configured to source a current I. A third current source 210c comprises four current sources connected in parallel, each configured to source a current I. A fourth current source 210d comprises eight current sources connected in parallel, each configured to source a current I. Further, each of the n P-FET current sources 210 is biased to a positive voltage+V and configured so as to source, when enabled, a current to the electrode node. The magnitude of the current for each of the n current sources is $2^n I$, where I is a fixed current reference value.

One or more additional P-FET current source(s) 212 may also be used, where each is configured to source a current $I/2^m$ to the electrode node 204, where m is an integer ranging form 1 to m. Such additional current sources, when used, are thus configured to source a current having a magnitude of I/2 (m=1), I/4 (m=2), I/8 (m=3), and so forth, up to $1/2^m$ (m=m), from the P-FET current sources. Alternatively, other P-FET current sources, not shown, could be used where each is configured to source a current I/m, where m is an integer equal to 2, 3, 4 . . . , or multiples of I/m.

Similarly, as seen in FIG. 3, a set 216 of n N-FET current sources 220a, 220b, 220c, 220d, . . . 220n, is also permanently connected to the electrode node 204. Each of the n N-FET current sources 220 comprises n individual current sources connected in parallel, each configured to sink a current I. That is, as seen in FIG. 3, each of the n N-FET current sources 220 is biased to sink a current from the electrode node 204, when enabled. The magnitude of the current that is sunk through each current source is $2^n I$, where I is a fixed current reference value.

One or more additional N-FET current source(s) 222 may also be used, where each is configured to sink a current $I/2^m$ to the electrode node 204, where m is an integer ranging form 1 to m. Such additional current sources, when used, are thus configured to sink a current having a magnitude of I/2 (m=1), I/4 (m=2), I/8 (m=3), and so forth, up to I/$2^m$ (m=m), from the N-FET current sources. Alternatively, other N-FET current sources, not shown, could be used where each is configured to sink a current I/m, where m is an integer equal to 2, 3, 4 . . . , or multiples of I/m.

Each of the current sources 210, 212, 220 and 222 is controlled by a respective bit signal, applied to the current source via a control line, which is used to selectively control which current sources are enabled, and which are not. Thus, for example, a bit signal "Bit+1" controls (enables) the P-FET current source 210a. Another bit signal, "Bit−1" controls the N-FET current source 220a. Similarly, a bit signal "Bit+2" controls the current source 210b; while a bit signal "Bit−2" controls the current source 220b. Other bit signals control the other current sources in a similar manner, with a "Bit+0" signal controlling the current source 212, and a "Bit−0" signal controlling the current source 222.

Thus, in order to program the output current source 200 to source or sink a desired current, all that need be done is to set the bit signals to the appropriate values. For example, setting the bit signals of the P-FET set 206 of current sources to "01110" in FIG. 3, where the left-most bit is the highest numbered bit (Bit 4) and the right-most bit is the lowest numbered bit (Bit 0), causes current source 212 to be disabled; current source 210a to be enabled so as to source a current I; current source 210b to be enabled so as to source a current 2I; current source 210c to be enabled so as to source a current 4I, and current source 210d to be disabled, thereby making a total current of I+2I+4I=7I to be sourced to the electrode node 204. At the same time that the P-FET current source set 206 is set to source a current of 7I to the electrode node 204, an N-FET current source set 216 associated with another electrode (an electrode that is to be paired with the electrode 202) is set to sink a current of 7I. In this way, a programmable current of, e.g., 7I is programmed to flow between the two paired electrodes.

Thus, it is seen that the output current source 200 shown in FIG. 3, in combination with similar current sources associated with other electrodes, may thus be programmed to source or sink any desired current value, from 0 to I/2 to $2^n$I, in increments of I/2, by simply setting the bit signals to appropriate values.

Further, the value of the current reference I may also be selected to be a desired value. In one embodiment, for example, the value of I may be set to 2.5 μa, 5.0 μa, 10.0 μa, or 20.0 μa. In another embodiment, the value of I may be set to be any summed combination of four current reference values, I1, I2, I3 and I4, i.e., the current reference I may be set to I1, I2, I1+I2, I3, I1+I3, I1+I2+I3, and so on, for all possible combinations of I1, I2, I3 and I4. For a cochlear stimulator, representative values for I1, I2, I3 and I4 for such embodiment are 2 μa, 4 μa, 8 μa, and 16 μa.

Biphasic current pulses may thus be readily generated using the output current source 200 shown in FIG. 3 by simply programming the appropriate P-FET set 206 of n current sources of a first selected electrode and the N-FET set 216 of n current sources of a second selected electrode (to be paired with the first selected electrode) to a desired amplitude value for a desired duration of the first portion of the biphasic pulse. Then, the polarity of the current sources is changed and the process repeated for a second portion of the biphasic pulse. Multiphasic current pulses may similarly be generated by programming appropriate amplitudes of the P-FET and N-FET current sources for appropriate periods of time. (Note, as used herein, "multiphasic" refers to a current pulse made up of a multiple current pulses of differing amplitudes, e.g., one or more current pulses of one polarity followed by one or more current pulses of the opposite polarity, with durations and amplitudes typically selected so that the net current flow, electrical charge per unit time, is zero. By way of example, a multiphasic current pulse may comprise an down-up stair-step type of waveform, e.g., a negative current pulse of 2 ma of 10 μsec duration, followed by a negative 4 ma current pulse of 10 μsec duration, followed by a negative 2 ma current pulse of 10 μsec duration, followed by a 0 ma current pulse of 10 μsec duration, followed by a positive current pulse of 2 ma of 10 μsec duration, followed by a positive 4 ma current pulse of 10 μsec duration, followed by a positive 2 ma current pulse of 10 μsec duration. Thus, in accordance with this definition, it is seen that a biphasic current pulse comprises one type of a multiphasic current pulse.)

If desired, unbalanced biphasic or multiphasic pulses (a first positive polarity portion having an amplitude and duration different from the amplitude and duration of a second negative polarity portion) may also be generated. However, in general, when stimulating living tissue, it is preferred that a biphasic or multiphasic stimulus pulse have a balanced charge, meaning that the amplitude-duration product of the positive polarity portions of the biphasic or multiphasic pulse be equal to the amplitude-duration product of the negative polarity portions of the biphasic or multiphasic pulse.

Figure 4:
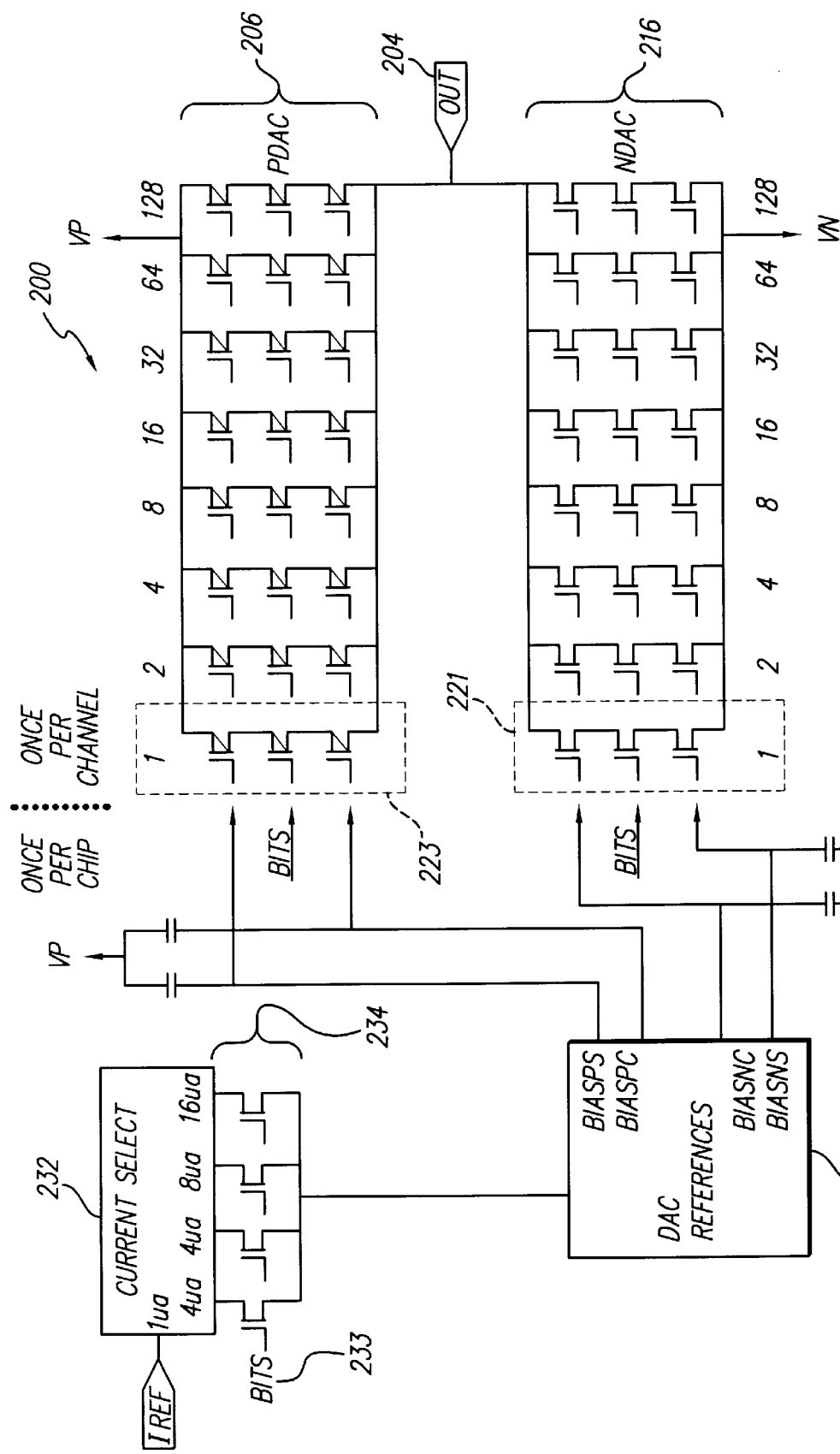
FIG. 4 is a block diagram of the programmable output current circuit of the present invention.

Turning next to FIG. 4, a block diagram of one embodiment of the programmable output current circuit 200 of the present invention is shown. As seen in FIG. 4, such embodiment includes an electrode node 204 to which is connected a set of P-FET current sources 206 and a set of N-FET current sources 216. As described above, the P-FET current sources source a selected current to the electrode node 204, while the N-FET current sources sink a selected current from the electrode node 204. For the embodiment shown in FIG. 4, the current sources within each set generate a current of I, 2I, 4I, 8I, 16I, 32I, 64I or 128I, as a function of the bit signals applied thereto. The P-FET set 206 of current sources may also be referred to as a "PDAC", or P-Digital-to-Analog Converter, because in combination they source a total current (an analog signal) having an amplitude determined by the bit signals (a digital signal). Similarly, the N-FET set 216 of current sources may likewise be referred to as an "NDAC", or N-Digital-to-Analog Converter, because in combination they sink a total current (an analog signal) having an amplitude determined by the bit signals (a digital signal).

As indicated above, each electrode has an electrode node 204 associated therewith, and each electrode node has a PDAC or NDAC permanently connected thereto. In order to provide appropriate bias signals, e.g., current reference signals, to the PDAC's and NDAC's so that they can perform their intended function, a DAC reference circuit 230 generates the needed reference signals. The reference circuit 230, in turn, receives a reference current value from a current select circuit 232. For the embodiment shown in FIG. 4, the current select circuit 232 allows any combination of four reference current values to be selected, through bit control signals 233 as applied to bit select circuit 234.

It is noted that the current select circuit 232, with its bit select circuit 234 and DAC reference circuit 230, as shown on the left-hand side of FIG. 4, need only be fabricated once per chip. The PDAC 206 and the NDAC 216, i.e., the circuitry on the right-hand side of FIG. 4, must be fabricated once for each electrode node. Typically, there will be a multiplicity of electrode nodes used with each stimulator, e.g., eight, twelve, sixteen, or twenty electrode nodes per chip.

Figure 5A:
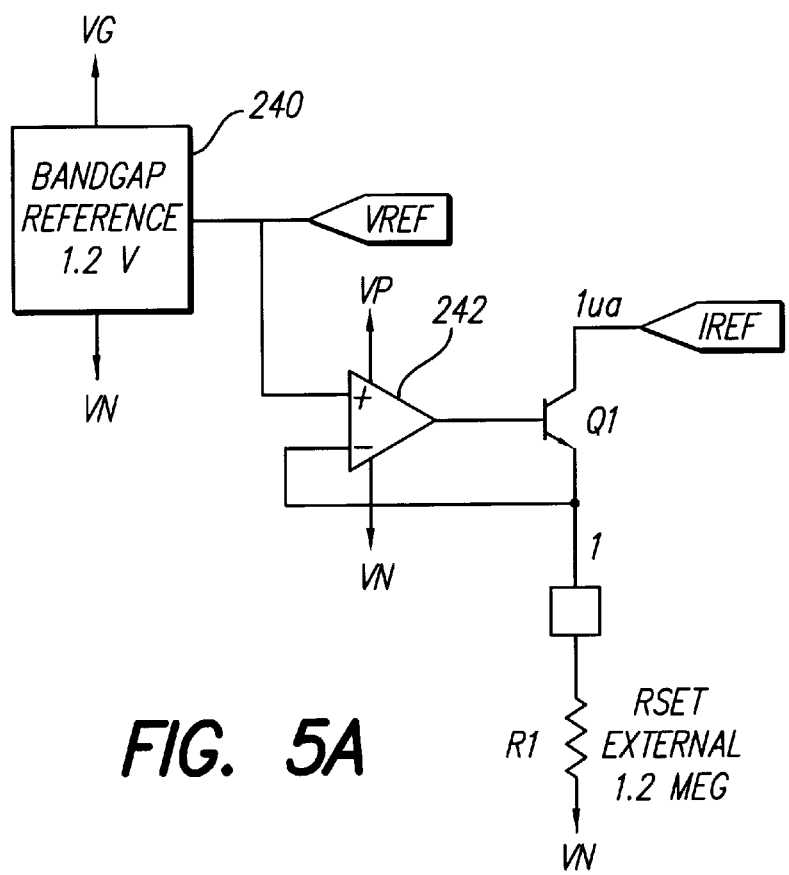
FIGS. 5A, 5B and 5C are block diagrams of the various regulators and reference circuits that are used with the programmable output current circuit of FIG. 4.
Figure 5C:
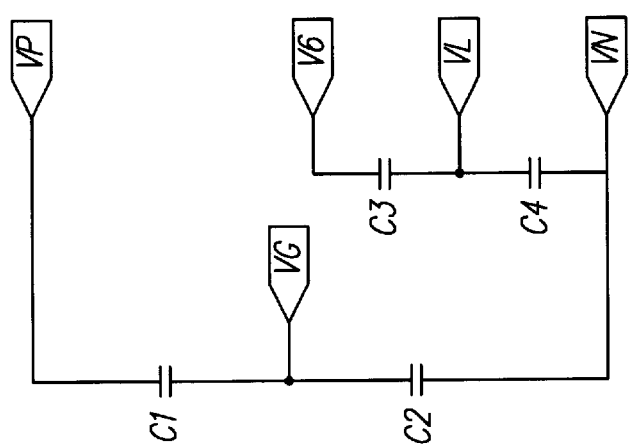
Figure 5B:
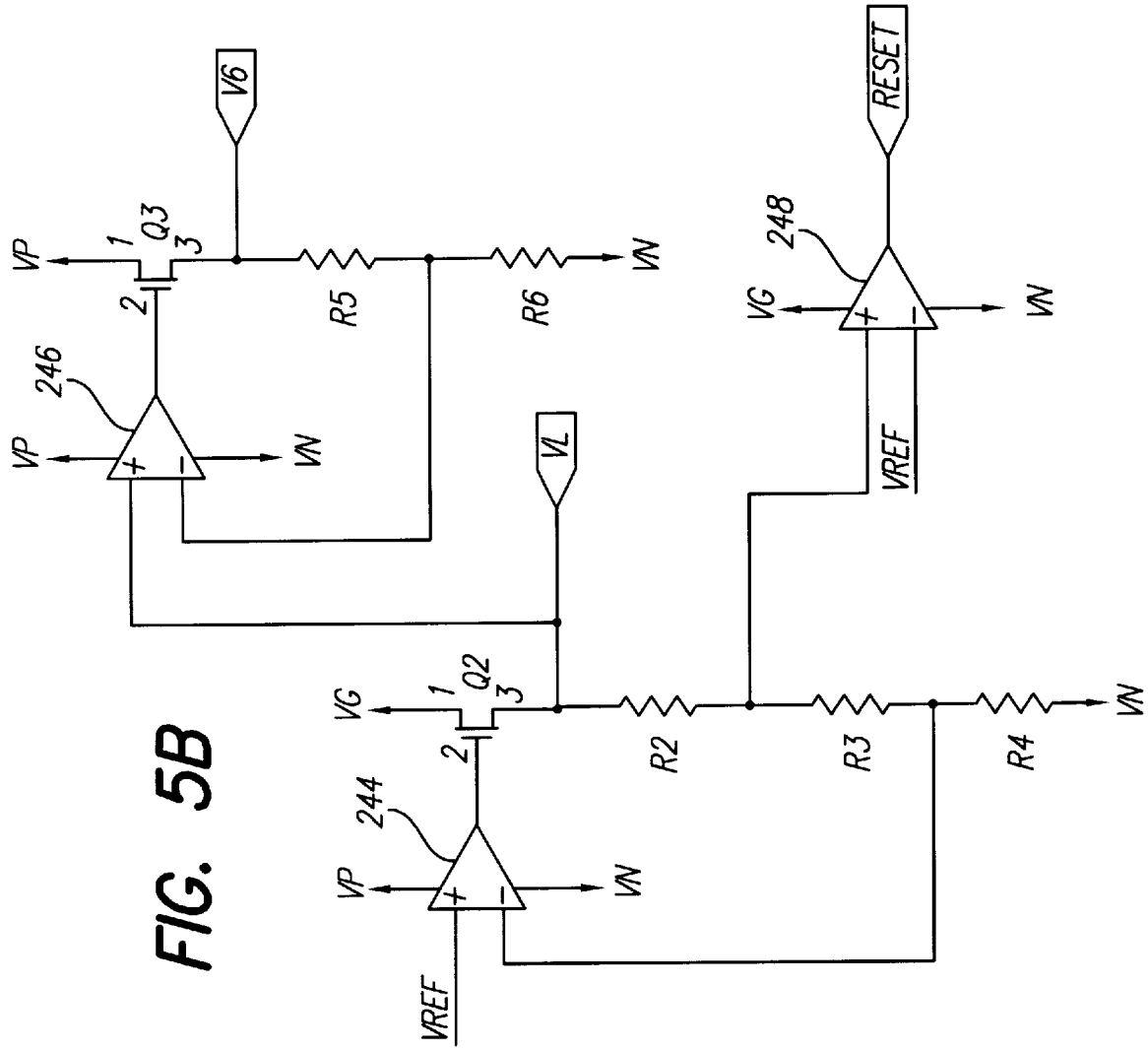

Turning next to FIGS. 5A, 5B and 5C, there are shown block diagrams of a preferred embodiment of the various voltage and/or current regulators and reference circuits that may be used with the programmable output current circuit of FIG. 4. In these figures, please note the following definitions:

- VN is the most negative power supply rail. The chip substrate is connected to VN, and VN is the negative rail for the logic, general analog, and stimulus circuits.
- VL is the logic power supply. VL is a regulated supply, 3 volts more positive than VN.
- V6 is a regulated supply six (6) volts more positive than VN. It is typically used as the positive supply rail of an A/D converter used with monitoring various signals on the chip.
- VG is the middle of the stimulus supply. VG is centered between VP and VN, and may thus sometimes be considered as electrical "ground".
- VP is the most positive supply rial. VP is used as the positive rail for stimulus output.
- VREF is a voltage reference derived from a bandgap circuit. It is nominally 1.2 volts more positive than VN
- IREF is a one (1) $\mu$a current provided as a reference to the Current Range Select circuit 222 (FIG. 4) of the stimulus PDAC 206 and NDAC 216.
- RESET- is an active low, logic level signal asserted when VL is less than 2.2 volts with respect to VN.

FIGS. 5A, 5B and 5C show a block diagram of one way in which the above-identified reference voltages and currents may be generated. In particular, FIG. 5A shows the use of a bandgap reference circuit 240 connected between VG and VN to generate VREF. The value of VREF, in turn, is then applied to an amplifier 242, connected between the supply rails VP and VN, which drives the base of transistor Q1. The emitter of transistor Q1 includes an external trim resistor R1, which is typically about 1.2 M$\Omega$., in order to generate the reference current IREF.

FIG. 5B illustrate one way in which the VL, V6 and RESET- signals are generated. As seen in FIG. 5B, operational amplifiers 244 and 246 are connected between the positive and negative supply rails VP and VN. A third operational amplifier 248 is connected between VG and VN. The reference signal VREF is applied to one input of amplifier 244, the output of which is connected to the gate of FET Q2. The drain of Q2 is connected to series-connected resistors R2, R3 and R4, thereby connecting this string of resistors between VG and VN. The node between resistors R3 and R4 provides a reference voltage that is applied to the other input of amplifier 244. The result is that the node between Q2 and R2 is driven to the desired reference voltage, VL (which is typically 3 volts more positive than VN).

As further seen in FIG. 5B, the reference voltage VL is applied as one of the inputs to amplifier 246. The output of amplifier 246 connects to the gate terminal of FET Q3. Q3 connects series-connected resistors R5 and R6 between VP and VN. The node between R5 and R6 is used as a feedback reference point to the other input of amplifier 246. The values of R5 and R6 are selected such that the reference voltage V6, which appears at the node between R5 and the drain of Q3, is driven to its desired value (six volts more positive than VN).

Still with reference to FIG. 5B, it is seen that the node between series-connected resistors R2 and R3 is used as a reference of VL which is applied to one of the inputs of amplifier 248. The other input of amplifier 248 is the signal RESET-, which signal assumes an active low whenever VL is less than about 2.2 volts with respect to VN.

FIG. 5C illustrates the relative relationship between the reference voltages VP, VG, V6, VL, and VN, and shows capacitors C1, C2, C3 and C4 which may be used to help regulate and filter each of these references. As seen in FIG. 5C, C1 and C2 are connected in series between the rail supply voltages VP and VN. The node between C1 and C2 is VG. Similarly, C3 and C4 are connected in series between VN and V6, with the node between C3 and C4 comprising the reference voltage VL.

From the above, it is seen that if VG is designated as zero volts, VP and VN are symmetrical about VG, with VP ranging from about +3.5 to +7 volts, and with VN ranging from −3.5 to −7 volts. VN, VL, and V6 form a tightly regulated supply triplet at VN, VN+3 and VN+6, respectively. VG and VP, on the other hand, vary with load and incoming power.

Figure 6:
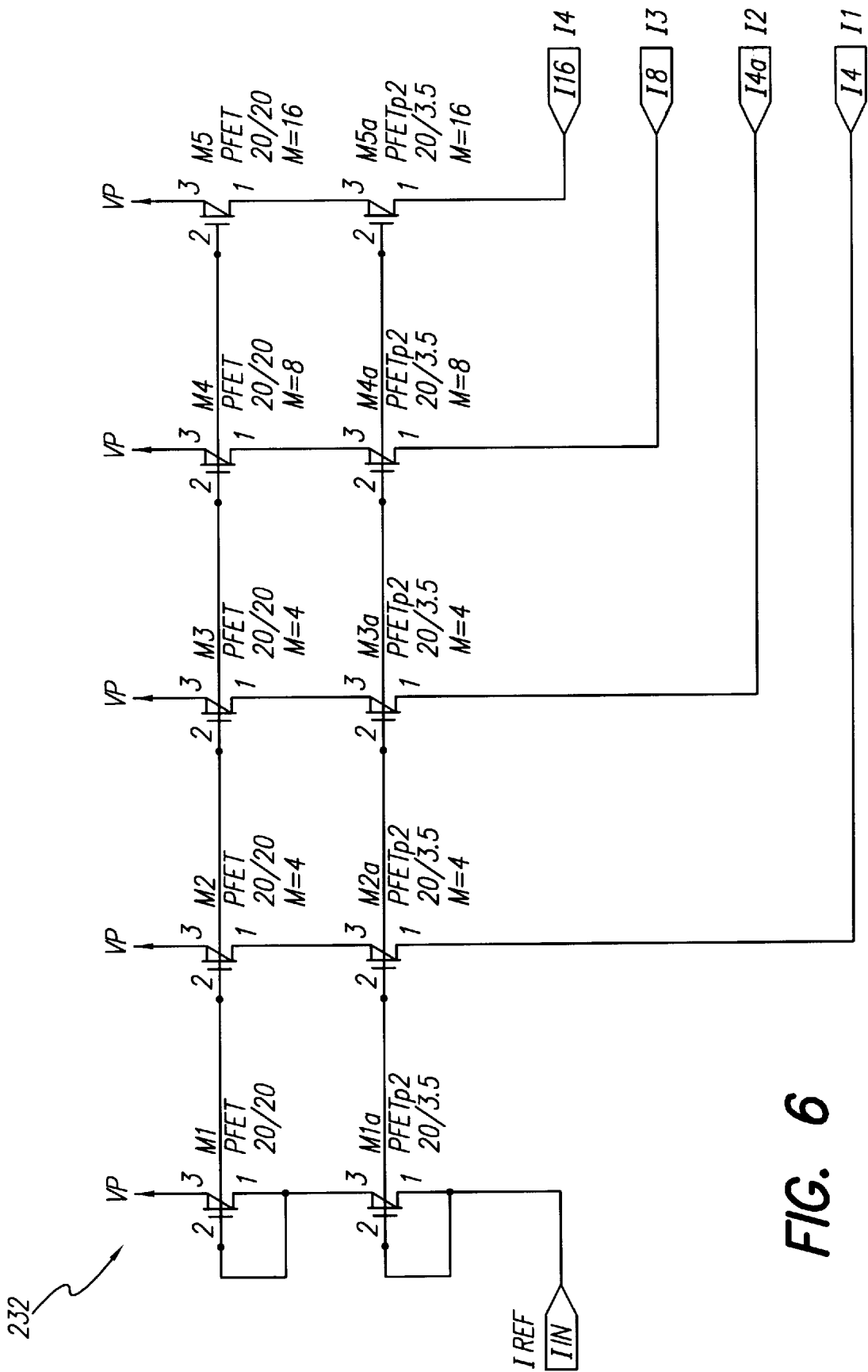
FIG. 6 is a schematic diagram of the current select circuit of FIG. 4.

FIG. 6 is a schematic diagram illustrating one manner in which the current select circuit 232 of FIG. 4 may be implemented using low power PFET transistors. Such low power transistors are formed on a common substrate, using conventional processing techniques, and are specifically designed for low power consumption. The preferred sizes (length and width) of each of the or PFET transistors are included in FIG. 6, along with other component values of interest. The length and width dimensions shown in FIG. 6 (and the other figures of this application that include similar information) relate to the relative size of each transistor as it is formed on the IC substrate.

More particularly, with reference to FIG. 6, for example, a PFET transistors having a size of "20/3.5" means that the width of the source to drain channel is 20 microns (where "micron" means one micrometer, also written as 1 $\mu$m, or 1$\times$10$^{-6}$ meters), and the length of the channel is 3.5 microns. Similarly, a size of "20/20" means that the width of the source to drain channel is 20 $\mu$m and the length of the channel is also 20 $\mu$m.

This type of characterization (by dimension or size) for the various PFET (or NFET) transistors used within an IC is known and understood by those of skill in the semiconductor processing art. Advantageously, by selectively controlling the size (dimensions) of such transistors during the IC processing steps, the performance of the FET transistors can be controlled or tailored for the specific design for which the transistor is used. Thus a relatively "long" NFET, having a size of, e.g., 5/10, may exhibit a higher turn-on resistance (and hence a slower turn on time) than would, e.g., a relatively "short" NFET, having a size of 4/4.

In general, as is known in the art, a FET transistor has three terminals, a "source", a "drain" and a "gate". The voltage applied to the gate terminal controls the conductivity of the semiconductor channel that connects the source and drain terminals. By controlling the conductivity of the source-drain channel, the amount of current that flows through the channel can be controlled, from zero current to a maximum current (determined by the ON resistance and the available voltage drop across the channel).

A common use for a FET transistor is as a switch. When used as a switch, the resistance of the source-drain channel, as controlled by the voltage applied to the gate terminal, is either very low (the FET switch is ON) or very high (the FET switch is OFF). In FIG. 6 (and other schematic diagrams presented herein) an NFET is depicted in classical FET form, i.e., appearing generally as a forward or backwards block letter "C", made up of three segments, with one end of one segment of the "C" comprising the "source", and with one end of another segment of the "C" (which end is marked with a heavy dot nearby) comprising the "drain". The "gate" is depicted as a short line that is parallel to, but not touching, the middle segment of the "C". A PFET is depicted the same as an NFET except that a diagonal line is drawn through the "C".

In FIG. 6, PFETs M1 and M1a are connected in series and are biased to have IREF flow therethrough. The gate of M1 creates a bias voltage that is also applied to the gates of M2, M3, M4 and M5. Each of these PFETs have the same dimensions as M1, but have a different "M" factor (or multiplication factor), which causes a current to flow through their respective source-drain channels that is a factor of M greater than the current IREF flowing through M1. Thus, where the M factor for M2 and M3 is "4", that means that each of the PFETs M2 and M3 have a current of 4IREF flowing therethrough. As seen in FIG. 6, the M factor for M4 is 8, and for M5 is 16. This means that so long as the gate voltage of these transistors is the same as the gate voltage applied to the PFET M1 (which has a current IREF flowing therethrough), the current flowing through PFET M4 will be 8IREF, and the current flowing through PFET M5 will be 16IREF.

In a similar manner, each of the PFETs M2a, M3a, M4a and M5 are biased to have a respective current I1, I2, I3 and I4 flow therethrough that is 4IREF, 4IREF, 8IREF and 16IREF, respectively.

Figure 7:
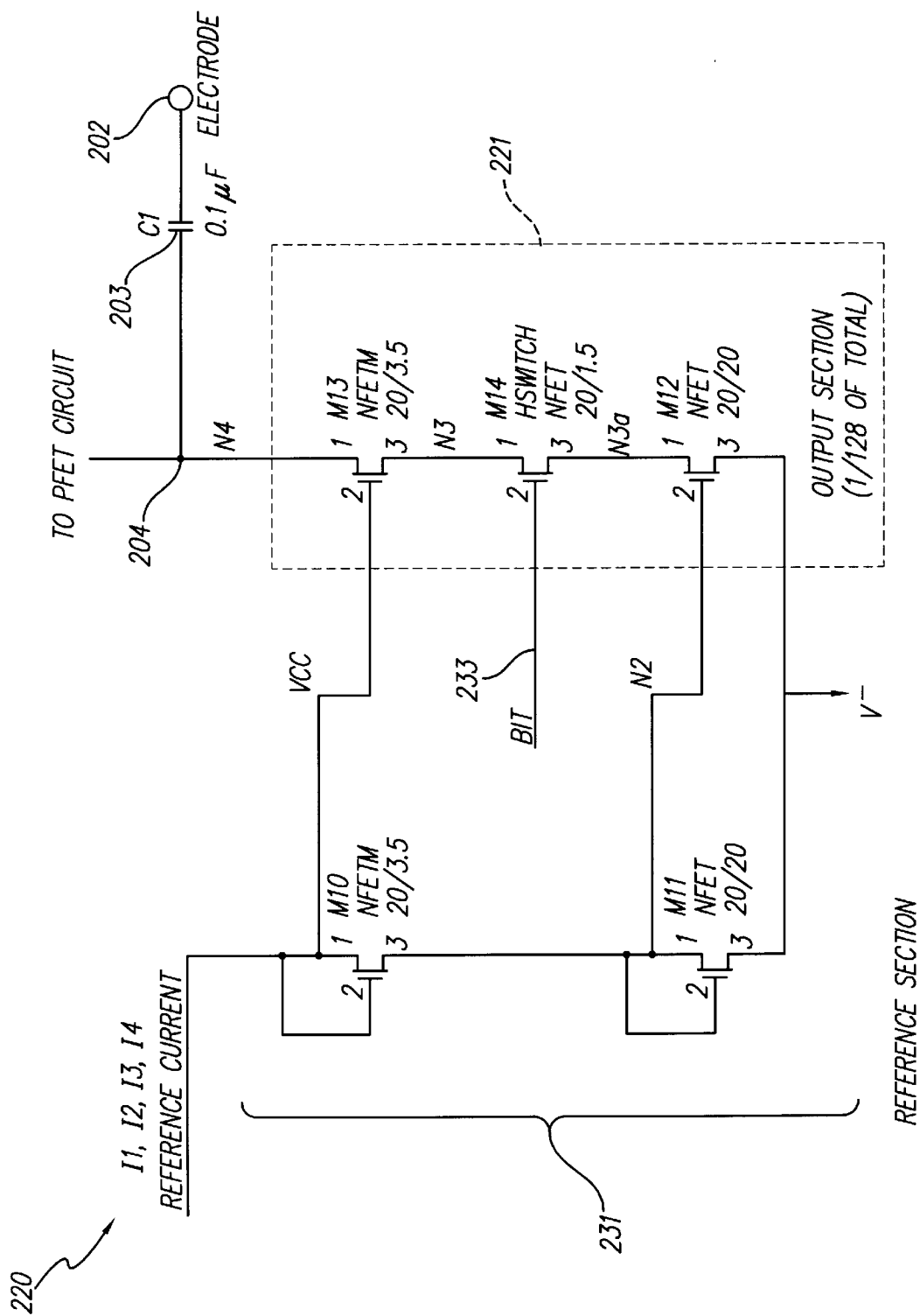
FIG. 7 is a schematic diagram of the basic current source circuit used within the programmable current circuit of FIG. 4.

FIG. 7 is a schematic diagram of the basic NFET current source circuit 220 that is used within the programmable current circuit 200 (FIG. 4) of the present invention. As seen in FIG. 7, such circuit 220 includes a reference section 231 and an output section 221. The reference section 231 may comprise part of the DAC reference circuit 230 (FIG. 4), which only need be fabricated once per chip; whereas the output section 221 comprises the fundamental building block of the NDAC circuit 216, and thus must be repeated many times for each electrode node.

The current output circuit 220 provides bi-directional currents into a stimulus electrode. Preferably, four full-scale current ranges are proposed, as determined by the values of I1, I2, I3 and I4 (or combinations thereof). For the configuration shown in FIG. 4, each range is spanned with 255 steps (8 bits).

It should be noted that variations of the configuration shown in FIG. 4 may also be used, e.g., where n full-scale current ranges are proposed, (where n is an integer) as determined by the values of I1, I2, I3, . . . In (or combinations thereof); and wherein each range is spanned by $2^m-1$ steps (m bits), e.g., where each of the n ranges is spanned by 1023 steps (10 bits).

As has been explained, each electrode node 204 is served by a pullup current source (PDAC 206) and a pulldown current source (NDAC 216). The pullup source is made of PFETs, and the pulldown source is made of NFETs. The circuit shown in FIG. 7 is off a portion of the NDAC circuit 216. The corresponding PFET circuit is similar, but wide PFETs are used because of the inherent lower conduction of the PFET.

With reference to FIG. 7 it is seen that the basic structure of the current source is a cascode mirror with a fixed size reference section 231 and multiple switchable output sections 221. The schematic shown in FIG. 7 includes the reference section 231, comprising PFETs M10 and M11, and the portion of the output section 221 which is responsible for 1/128th of the full scale current. That is, the output section 221 shown in FIG. 7 corresponds to bit 1, where bit 0 is the least significant bit (lsb), and where the lsb is realized using the I/2 current source 222 (FIG. 3).

The cascode structure illustrated in FIG. 7 provides a current which is nearly independent of the output voltage. The reference current I1, I2,I3 or I4, flows through both M10 and M11. M11 provides a reference voltage at node N2 which causes M12 to have a similar current. However, the current flowing through M12 will only match well if the drain voltage of M12 is near that of M11. M10 provides a voltage at node VGC which biases M13 such that the drain of M12 is indeed held at a voltage near the drain of M11 over most of the output voltage range. The tracking is not perfect, therefore both M11 and M12 have relatively long channels (20 $\mu$m) to reduce the dependence of their drain currents on drain voltages.

To increase the maximum output voltage, M10 and M13 are thick oxide (poly 2) FETS. Their cascode operation prevents the thin oxide FETS (M11 and M12) from ever having a high drain voltage. The thin oxide NFET MSWITCH M14 turns this section of the output circuit ON and OFF according to the control BIT signal, applied to signal line 233.

With the cascode arrangement shown in FIG. 7, the output current tracks the reference current over a wide voltage range.

Figures 1, 8A:
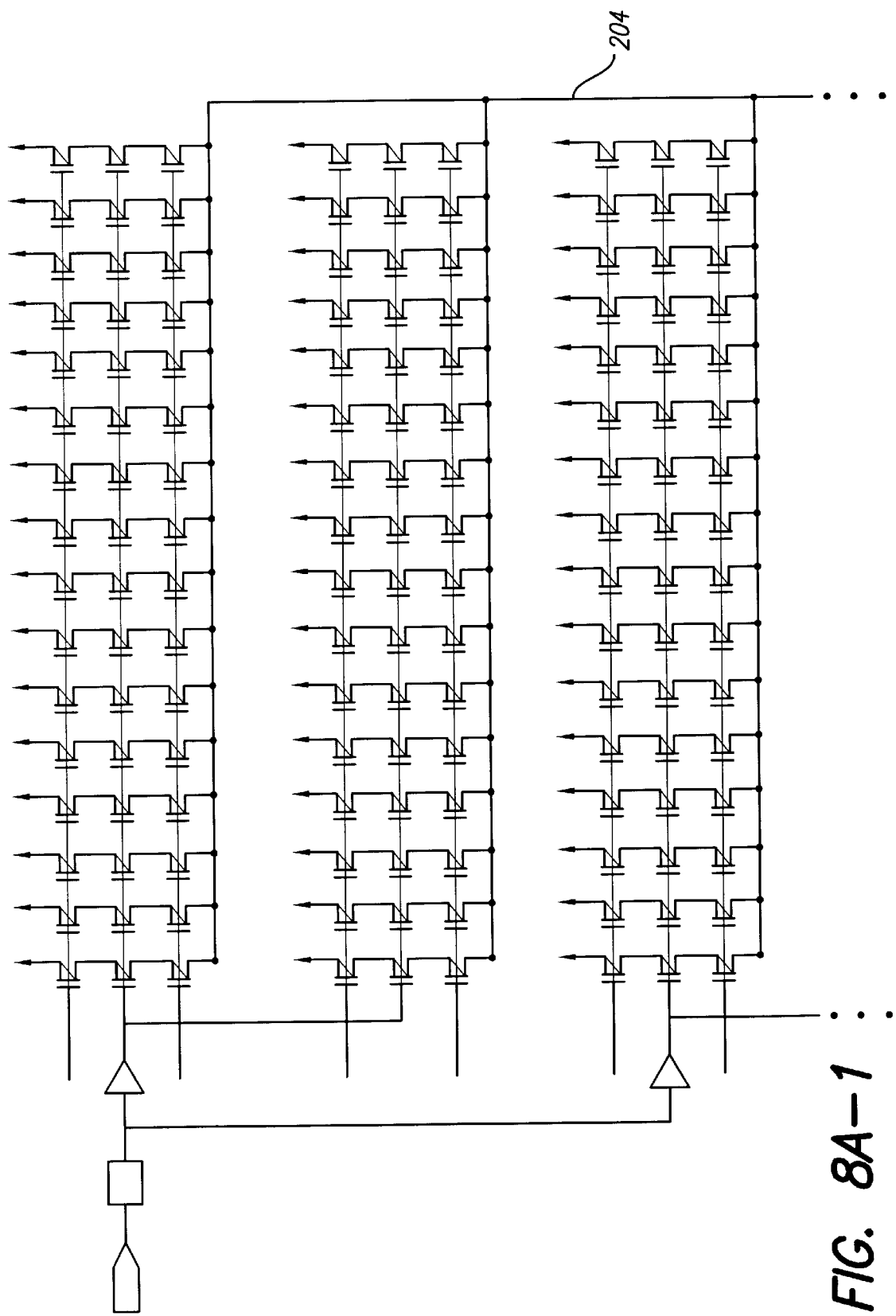
FIGS. 8A and 8B are schematic/block diagrams of a preferred embodiment of the programmable output current circuit of FIG. 4.
Figures 2, 8A:
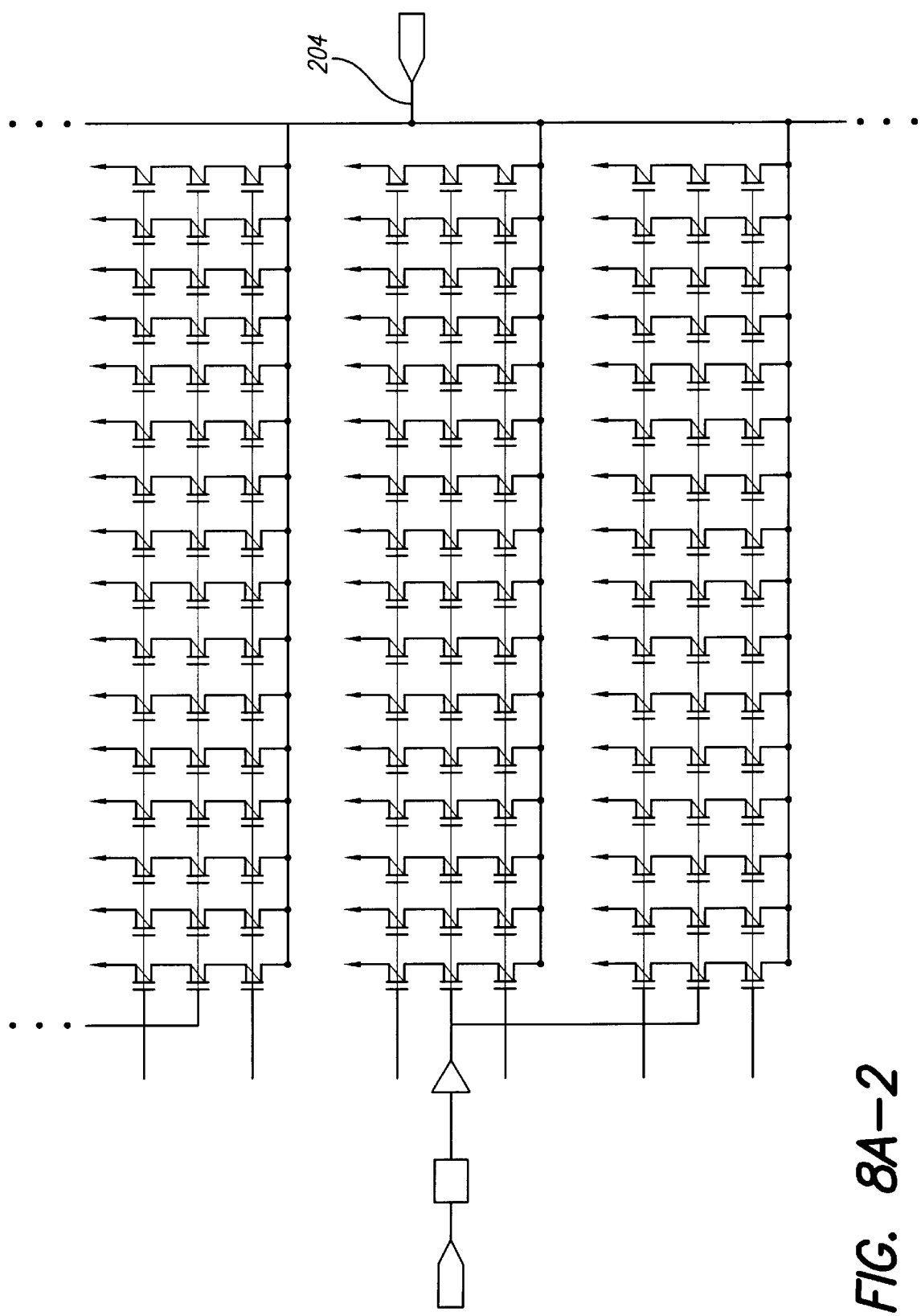
Figures 3, 8A:
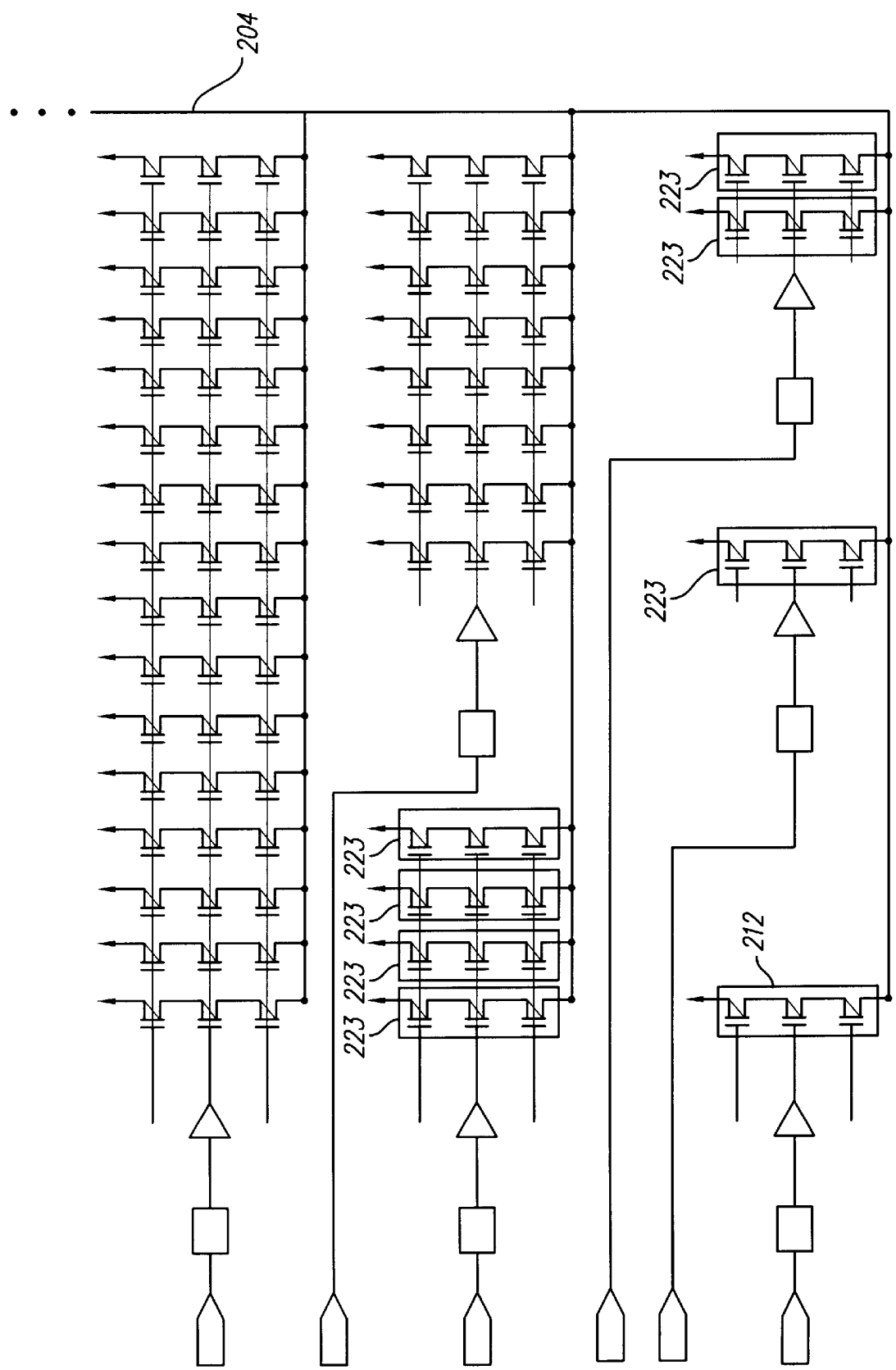
Figures 1, 8B:
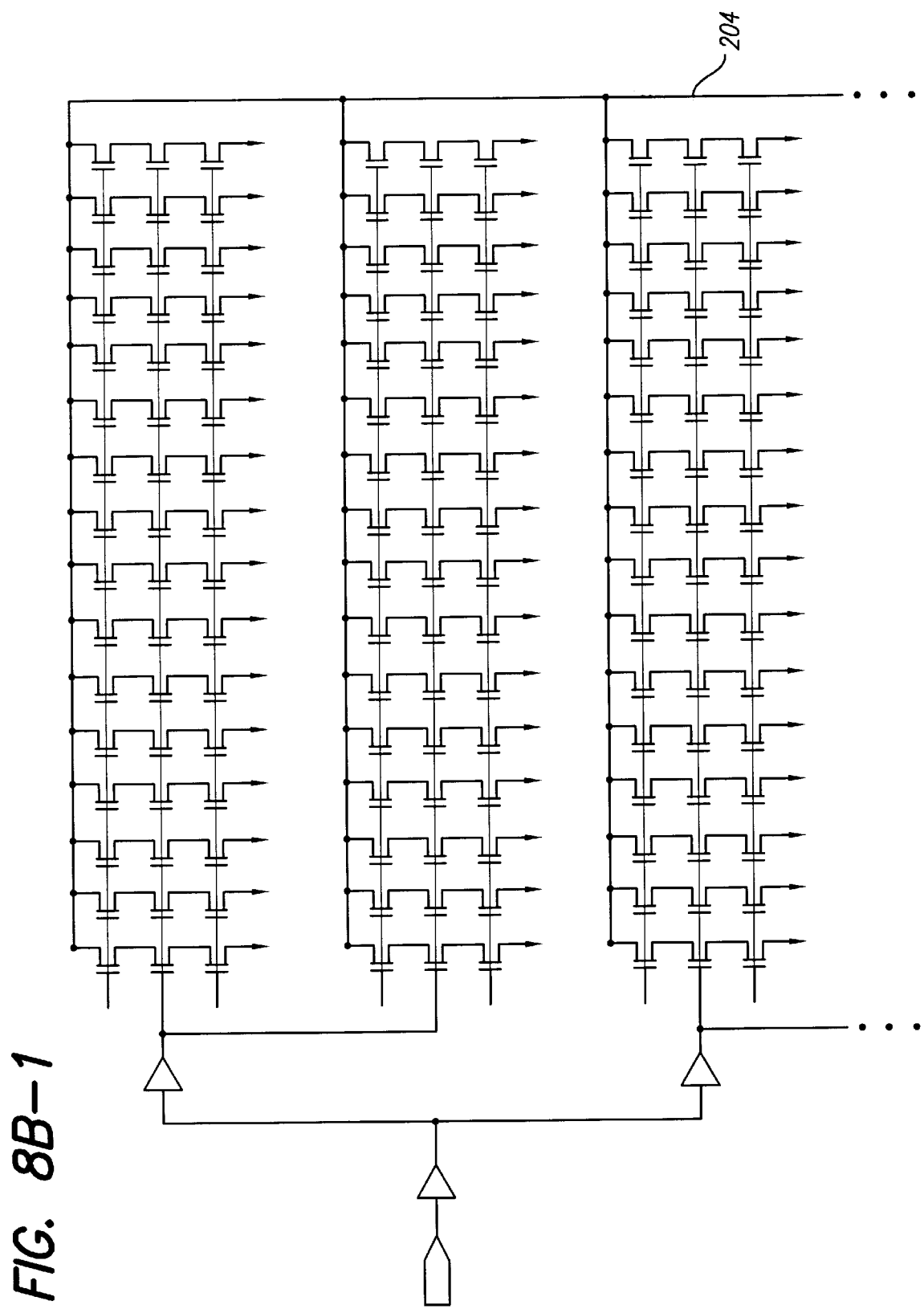
Figures 2, 8B:
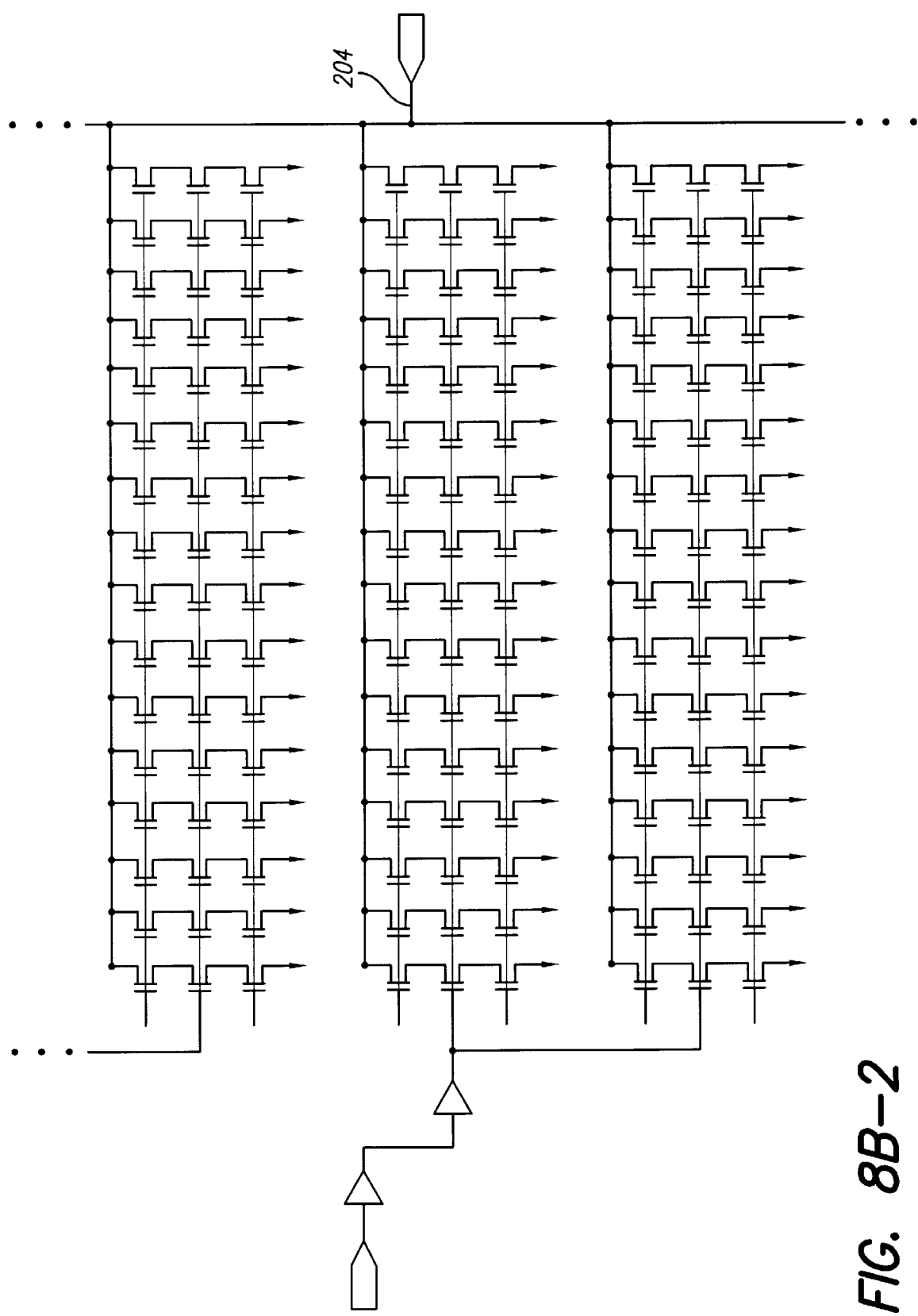
Figures 3, 8B:
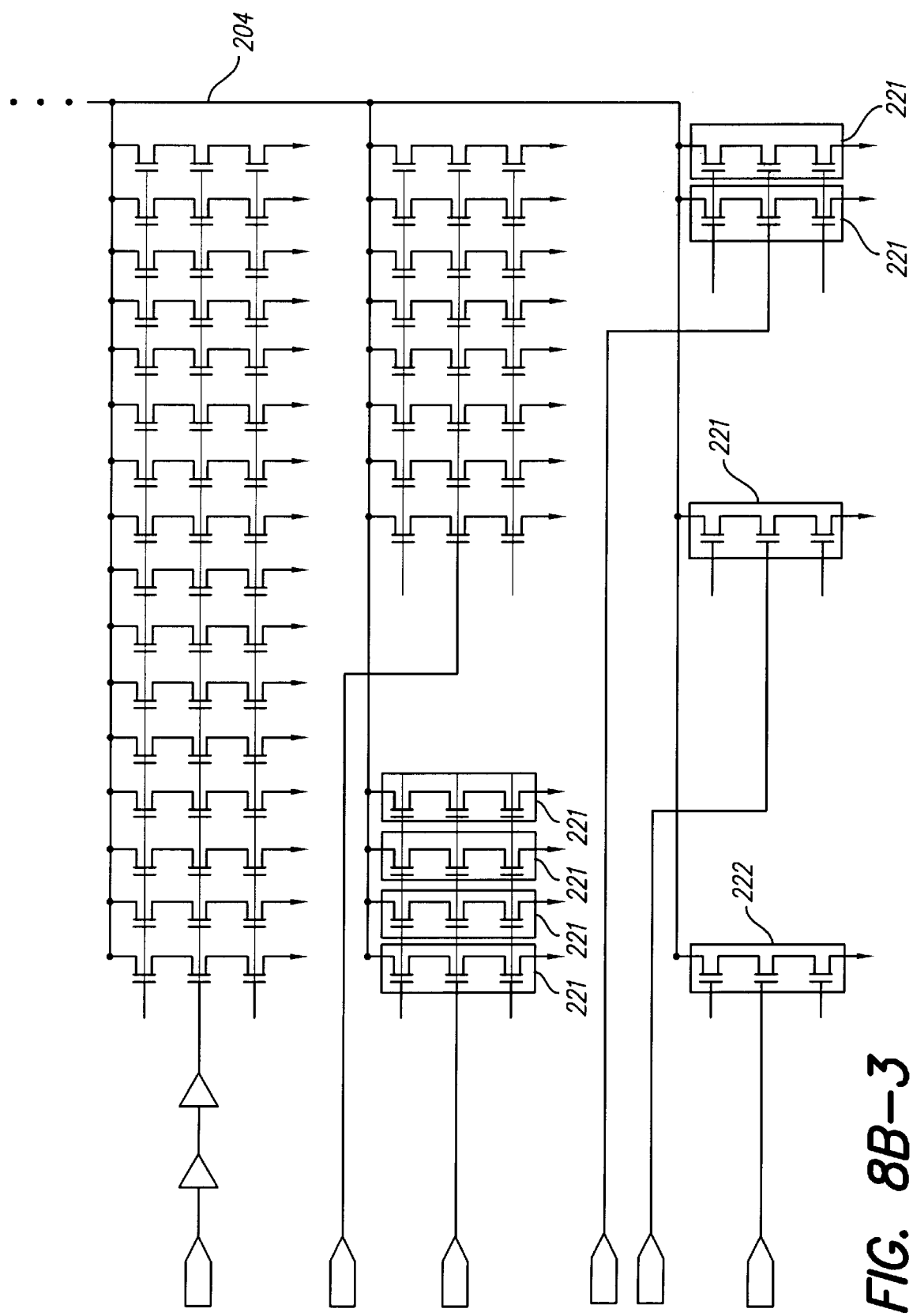

FIGS. 8A and 8B are schematic/block diagrams of a preferred embodiment of the programmable output current circuit of FIG. 4. As evident from FIG. 8B, for example, the programmable output NFET current circuit comprises the output portion 221 (FIG. 7), configured to pulldown the current I, repeated as necessary to provide the desired total pulldown current at the electrode node 204. Thus, bit 1 connects to the circuit 221. Bit 2 connects to two of the circuits 221 connected in parallel. Bit3 connects to four of the circuits 221 connected in parallel, and so on, through all eight bits. Bit 0 connects to the circuit 222 (which pulls down I/2).

In a similar manner, the programmable output PFET current circuit comprises the output portion 223 (FIG. 4), configured to pullup the current I, repeated as necessary to provide the desired total pullup current at the electrode node 204. Thus, bit 1 connects to the circuit 223. Bit 2 connects to two of the circuits 223 connected in parallel. Bit3 connects to four of the circuits 223 connected in parallel, and so on, through all eight bits. Bit 0 connects to the circuit 212 (which pulls up I/2).

From the above, it is thus seen that the invention provides an output current source circuit for each electrode of an implantable tissue or nerve stimulator that selectively sources (pulls up) or sinks (pulls down) a current having a programmable amplitude to the electrode node, while at all times remaining permanently connected to the electrode node.

It is further seen that the invention provides such an output current source circuit that may be fabricated using low power CMOS N-FET and P-FET transistors.

While the invention herein disclosed has been described by means of specific embodiments and applications thereof, numerous modifications and variations could be made thereto by those skilled in the art without departing from the scope of the invention set forth in the claims.

What is claimed is:

1. A programmable output current circuit for use within an implantable medical device having a plurality of stimulus electrodes, a selected grouping of said stimulus electrodes providing a path through which a programmable stimulus current is selectively applied, each of the plurality of electrodes having an electrode node associated therewith, the programmable output current circuit for each electrode node comprising:

a set of n P-FET current sources, where n is an integer equal to 0, 1, 2, . . . n, wherein each of the n P-FET current sources is permanently attached to the electrode node, and further wherein each of the n P-FET current sources is biased to source a current to the electrode node having a programmable value of $2^nI$ where I is a fixed current reference value; and a set of n N-FET current sources, wherein each of the n N-FET current sources is also permanently attached to the electrode node, and further wherein each of the n N-FET current sources is biased to sink a current from the electrode node having a programmable value of $2^nI$; and control means for selectively biasing each of the n P-FET and n N-FET current sources in an enabled or disabled state;

an electrode associated with each electrode node;

wherein a first combination of enabled P-FET current sources, accompanied by a second combination of enabled N-FET current sources, cause a current flow to occur through a load connected between the electrodes associated with the electrode nodes of the respective sets of enabled P-FET and N-FET current sources having a magnitude equal to the sum of all the currents sourced from each of the enabled P-FET current sources, which sum is equal to the sum of all the currents sunk to each of the enabled N-FET current sources.

2. The programmable output current circuit of claim 1 wherein the value of I is programmable to assume one of four values: I1, I2, I3 or I4.

3. The programmable output current circuit of claim 2 wherein I4=2I3=4I2=8I1.

4. The programmable output current circuit of claim 3 wherein I4=20 μa.

5. The programmable output current circuit of claim 1 wherein the value of I is determinable from various combinations of four current values: I1, I2, I3 or I4.

6. The programmable output current circuit of claim 4 wherein I4=2I3=4I2=4I1.

7. The programmable output current circuit of claim 5 wherein I4=16 μa.

8. The programmable output current circuit of claim 1 wherein n equals eight, whereby the current flow may be programmed to assume values of from I to 128I in increments of I.

9. The programmable output current circuit of claim 1 further including at least one additional P-FET current source connected to the electrode node, said at least one additional P-FET current source sourcing a current equal to a fraction of I, and at least one additional N-FET current source connected to the electrode node, said at least one additional N-FET current source sinking a current equal to the same fraction of I.

10. The programmable output current circuit of claim 9 wherein the at least one additional P-FET current source sources a current equal to $I/2^m$, where m is an integer having values of 1, 2, 3, . . . m, and wherein the at least one additional N-FET current source sinks a current equal to $I/2^m$.

11. The programmable output current circuit of claim 9 wherein three additional P-FET current sources are connected to the electrode node, a first sourcing a current of I2 to the electrode node when enabled, a second sourcing a current of I/4 to the electrode node when enabled, and a third sourcing a current of I/8 to the electrode node when enabled; and further wherein three additional N-FET current sources are connected to the electrode node, a first sinking a current of I2 from the electrode node when enabled, a second sinking a current of I/4 from the electrode node when enabled, and a third sinking a current of I/8 from the electrode node when enabled.

12. The programmable output current circuit of claim 1 wherein a first P-FET current source corresponding to n=1 comprises a basic current source that includes first, second, and third P-FET CMOS transistors connected in series, the first and third P-FET CMOS transistors being biased to have the current I flow therethrough, the second P-FET transistor having a bit control signal applied thereto that either disables or enables the second P-FET transistor; and a first N-FET current source for n=1 comprises a basic current source that includes first, second, and third N-FET CMOS transistors connected in series, the first and third N-FET CMOS transistors being biased to have the current I flow therethrough, the second N-FET transistor having a bit control signal applied thereto that either disables or enables the second N-FET transistor.

13. The programmable output current circuit of claim 12 wherein the second P-FET current source corresponding to n=2 comprises two of the first P-FET current sources corresponding to n=1 connected in parallel, and wherein the third P-FET current source corresponding to n=3 comprises four of the first P-FET current sources corresponding to n=1 connected in parallel, and wherein the fourth P-FET current source corresponding to n=4 comprises eight of the first P-FET current sources corresponding to n=1 connected in parallel, and so on, with the nth P-FET current source comprising $2^{(n-1)}$ P-FET current sources corresponding to n=1 connected in parallel.

14. The programmable output current circuit of claim 12 wherein the second N-FET current source corresponding to n=2 comprises two of the first N-FET current sources corresponding to n=1 connected in parallel, and wherein the third N-FET current source corresponding to n=3 comprises four of the first N-FET current sources corresponding to n=1 connected in parallel, and wherein the fourth N-FET current source corresponding to n=4 comprises eight of the first N-FET current sources corresponding to n=1 connected in parallel, and so on, with the nth N-FET current source comprising $2^{(n-1)}$ N-FET current sources corresponding to n=1 connected in parallel.

15. A programmable output current stage for use within an implantable medical device having a plurality of stimulus electrodes, a selected grouping of said stimulus electrodes providing a path through which a programmable stimulus current is selectively applied to body tissue adjacent the stimulus electrodes, each of the plurality of electrodes having an electrode node associated therewith, the programmable output current stage comprising a plurality of positive and negative programmable current sources attached to each electrode node, the plurality of positive and negative programmable current sources attached to each electrode node comprising:

a first set of n positive current sources, where n is an integer equal to 0, 1, 2, . . . n, wherein each of the n positive current sources is permanently attached to the electrode node, and further wherein each of the n positive current sources is biased, when enabled, to source a current to the electrode node having a magnitude of $2^n I$, where I is a fixed current reference value, and a second set of n negative current sources, wherein each of the n negative current sources is also permanently attached to the electrode node, and further wherein each of the n negative current sources is biased, when enabled, to sink a current from the electrode node having a magnitude of $2^n I$, and a respective control line attached to each of the n positive and negative current sources, wherein a control signal applied to the control line enables or disables the current source to which the control line is attached; and an electrode associated with each electrode node;

wherein a first combination of enabled positive current sources, accompanied by a second combination of enabled negative current sources, causes a current flow to occur through body tissue adjacent the electrodes associated with the electrode nodes of the enabled positive and negative current sources.

16. The programmable output current stage of claim 15 further including at least one additional positive current source connected to the electrode node, wherein said at least one additional positive current source, when enabled, sources a current to the electrode node equal to a fraction of I, and further including at least one additional negative current source connected to the electrode node, wherein said at least one additional negative current source, when enabled, sinks a current from the electrode node equal to the same fraction of I.

17. The programmable output current stage of claim 16 wherein the fraction of I sourced and sunk, respectively, by the at least one positive and negative current sources comprises $I2^m$, where m is an integer having values of 1, 2, 3, . . . m.

18. A programmable output current circuit (200) connected to each electrode node (204) of an multi-electrode node implantable medical stimulator, comprising:

a set of P-FET current sources (206) permanently connected to the electrode node; and a set of N-FET current sources (216) permanently connected to the electrode node;

wherein the P-FET current sources, when enabled, source a programmed current to the electrode node, and wherein the N-FET current sources, when enabled, sink he programmed current from the electrode node 204.

19. The programmable output current circuit of claim 18 wherein the current sources within the set of P-FET current sources each generate a current of I, 2I, 4I, 8I, 16I, 32I, 64I or 128I, as a function of digital bit signals applied thereto; and wherein the current sources within the set of N-FET current sources each generate a current of I, 2I, 4I, 8I, 16I, 32I, 64I or 128I, as a function of digital bit signals applied thereto;

wherein the current sources that source current function as a P-Digital-to-Analog Converter (PDAC) because in combination they source a total current, which comprises an analog signal, having an amplitude determined by the digital bit signals applied thereto, and wherein the current sources that sink current function as an N-Digital-to-Analog Converter (NDAC) because in combination they sink a total analog current having an amplitude determined by the digital bit signals applied thereto.

20. The programmable output current circuit of claim 19 further including at least one additional current source within the PDAC that generates a current that is a fraction of I, and at least one additional current source within the NDAC that likewise generates a current that is the same fraction of I.

* * * * *